US012208008B2

(12) United States Patent
Eggert et al.

(10) Patent No.: US 12,208,008 B2
(45) Date of Patent: Jan. 28, 2025

(54) EDGE TO EDGE REPAIR DEVICE FOR VALVES

(71) Applicant: Boston Scientific Scimed, Inc., Maple Grove, MN (US)

(72) Inventors: Joel T. Eggert, Plymouth, MN (US); Aaron Abbott, Columbia Hieghts, MN (US); James P. Rohl, Prescott, WI (US); Daniel Shuey, Pine City, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 896 days.

(21) Appl. No.: 17/115,032

(22) Filed: Dec. 8, 2020

(65) Prior Publication Data

US 2021/0169651 A1 Jun. 10, 2021

Related U.S. Application Data

(60) Provisional application No. 62/945,453, filed on Dec. 9, 2019.

(51) Int. Cl.
*A61F 2/24* (2006.01)
*A61F 2/00* (2006.01)

(52) U.S. Cl.
CPC .......... *A61F 2/2463* (2013.01); *A61F 2/2466* (2013.01); *A61F 2002/0086* (2013.01); *A61F 2220/0016* (2013.01)

(58) Field of Classification Search
CPC ............ A61B 17/12122; A61B 17/122; A61B 17/1227; A61F 2/2442; A61F 2/2466; A61F 2/2463; A61F 2220/0016
See application file for complete search history.

(56) References Cited

U.S. PATENT DOCUMENTS

| 7,736,388 | B2 | 6/2010 | Goldfarb et al. |
| 8,052,592 | B2 | 11/2011 | Goldfarb et al. |
| 8,216,230 | B2 | 7/2012 | Hauck et al. |
| 8,252,050 | B2 | 8/2012 | Maisano et al. |
| 9,011,468 | B2 | 4/2015 | Ketai et al. |

(Continued)

FOREIGN PATENT DOCUMENTS

| EP | 3277200 A1 | 2/2018 |
| EP | 3481303 A1 | 5/2019 |
| WO | 2018093663 A1 | 5/2018 |

*Primary Examiner* — William H Matthews
(74) *Attorney, Agent, or Firm* — Seager, Tufte & Wickhem, LLP

(57) ABSTRACT

A valve fixation device may comprise a unitary elongate member that is biased towards a closed configuration wherein at least a pair of tissue engaging surfaces of the elongate member are held adjacent to each other by a bias force. The bias force is at least equal to a valve leaflet grasping force, enabling the fixation device to grasp and retain leaflets as part of cardiac treatment. A delivery tool including a spreader may independently translate the tissue engaging surfaces to enable cardiac leaflets to be captured and retained by and/or between the tissue engaging surfaces. The valve fixation device may include at least two arms, each of which may be independently controlled to grasp and capture opposing leaflets of a valve, such as the anterior and posterior leaflets of a mitral valve, to reduce the size of the valve opening and improve cardiac performance.

20 Claims, 12 Drawing Sheets

(56) References Cited

U.S. PATENT DOCUMENTS

| | | |
|---|---|---|
| 9,060,858 B2 | 6/2015 | Thornton et al. |
| 9,510,829 B2 | 12/2016 | Goldfarb et al. |
| 9,510,837 B2 | 12/2016 | Seguin |
| 9,572,666 B2 | 2/2017 | Basude et al. |
| 9,681,864 B1 | 6/2017 | Gammie et al. |
| 10,076,327 B2 | 9/2018 | Ellis et al. |
| 10,136,993 B1 | 11/2018 | Metchik et al. |
| 10,149,685 B2 | 12/2018 | Kizuka |
| 10,188,392 B2 * | 1/2019 | Wei .................. A61F 2/246 |
| 10,226,309 B2 | 3/2019 | Ho et al. |
| 10,238,494 B2 | 3/2019 | McNiven et al. |
| 10,238,495 B2 | 3/2019 | Marsot et al. |
| 2007/0118151 A1 | 5/2007 | Davidson |
| 2009/0105729 A1 | 4/2009 | Zentgraf |
| 2011/0060407 A1 | 3/2011 | Ketai et al. |
| 2013/0338764 A1 * | 12/2013 | Thornton .............. A61B 17/08 623/2.11 |
| 2015/0250590 A1 | 9/2015 | Gries et al. |
| 2016/0367787 A1 | 12/2016 | Van Hoven et al. |
| 2017/0020521 A1 | 1/2017 | Krone et al. |
| 2017/0035566 A1 | 2/2017 | Krone et al. |
| 2017/0252032 A1 | 9/2017 | Hiorth et al. |
| 2018/0036119 A1 | 2/2018 | Wei et al. |
| 2018/0092661 A1 | 4/2018 | Prabhu |
| 2018/0125658 A1 | 5/2018 | Prabhu |
| 2018/0133007 A1 | 5/2018 | Prabhu |
| 2018/0133010 A1 | 5/2018 | Kizuka |
| 2018/0146966 A1 | 5/2018 | Hernandez et al. |
| 2018/0161035 A1 | 6/2018 | Greenberg et al. |
| 2018/0161159 A1 | 6/2018 | Lee et al. |
| 2018/0185153 A1 | 7/2018 | Bishop et al. |
| 2018/0303614 A1 | 10/2018 | Schaffner et al. |
| 2018/0325671 A1 | 11/2018 | Abunassar et al. |
| 2018/0353181 A1 | 12/2018 | Wei |
| 2018/0353182 A1 | 12/2018 | Wei |
| 2019/0030285 A1 | 1/2019 | Prabhu et al. |
| 2019/0150926 A1 | 5/2019 | Greenberg et al. |
| 2019/0151041 A1 | 5/2019 | Ho et al. |

* cited by examiner

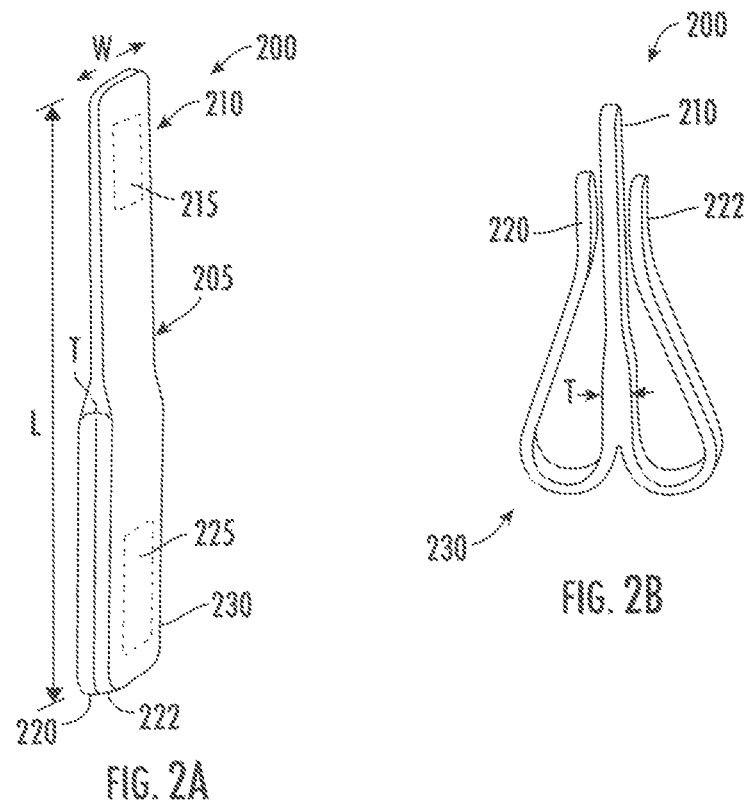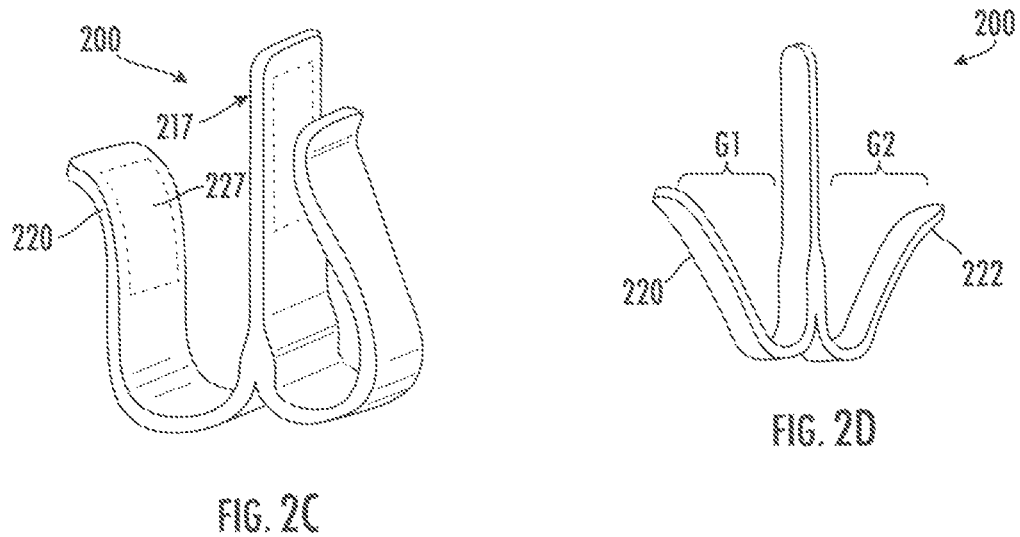
FIG. 2A
FIG. 2B
FIG. 2C
FIG. 2D

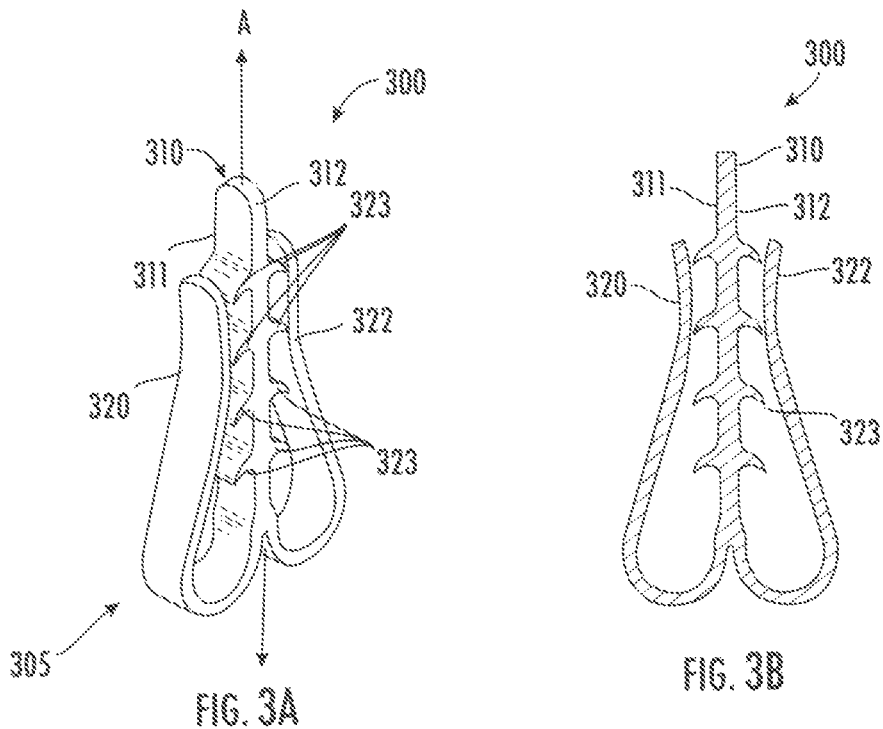
FIG. 3A
FIG. 3B
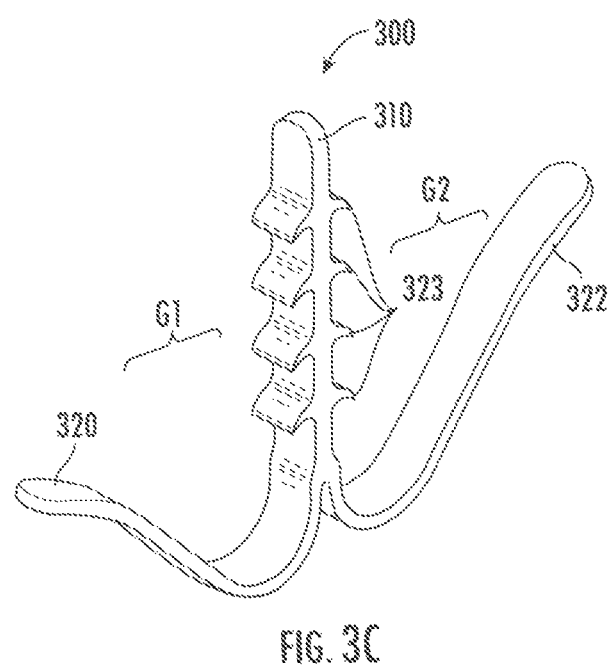
FIG. 3C

EDGE TO EDGE REPAIR DEVICE FOR VALVES

CROSS-REFERENCE TO RELATED APPLICATIONS

The present application claims the benefit of priority under 35 U.S.C. § 119 to U.S. Provisional Patent Application No. 62/945,453, filed Dec. 9, 2019, which application is incorporated herein by reference in its entirety for all purposes.

FIELD

The present disclosure relates generally to the field of implantable medical devices. In particular, the present disclosure relates to medical devices, systems, and methods for cardiac treatment.

BACKGROUND

Mitral regurgitation occurs when the native mitral valve fails to close properly, causing blood to flow back into the left atrium from the left ventricle during the systolic phase of heart contraction. Mitral regurgitation may have many causes, including but not limited to leaflet prolapse, dysfunctional or damaged papillary muscles, congenital defects, rheumatic fever, and/or stretching of a valve annulus. Mitral regurgitation can interrupt the body's ability to effectively process oxygen, causing fatigue and lightheadedness. Over time, regurgitation may lead to enlargement of the left atrium and compromised heart function.

SUMMARY

According to one aspect, a leaflet fixation device includes a unitary elongate body including a proximal neck portion including a first tissue engaging surface and a distal portion including an arm having a second tissue engaging surface. The arm may include an open configuration where the first tissue engaging surface may be spaced away from the second tissue engaging surface, the arm being biased towards a closed configuration where the second tissue engaging surface may be retained adjacent to the first tissue engaging surface by a bias force, and where the bias force may be at least equal to a leaflet grasping force.

In various embodiments, the arm may be one of a plurality of arms biased towards the closed configuration and in the closed configuration and each arm of the unitary elongate body may be adjacent to a different part of the proximal neck portion of the unitary elongate body. In one embodiment, in the closed configuration, a first arm may be adjacent to a first surface of the proximal neck portion of the unitary elongate body and a second arm may be adjacent to a second, opposing surface of the proximal neck portion of the unitary elongate body. In various embodiments, the proximal neck portion, the distal portion, or both may include a tissue retention feature. The tissue retention feature may be one of a plurality of tissue retention features disposed on the proximal neck portion, the distal portion or a combination of the proximal neck portion and the distal portion and configured to penetrate but not puncture tissue, puncture tissue or both.

The tissue retention feature may include a barb, a hook, a tooth, a tine or a combination thereof. The tissue retention feature may include a feature that promotes tissue ingrowth into the unitary elongate body. Each arm of the plurality of arms may be configured to move independently from other arms of the plurality of arms. In one embodiment, the unitary elongate body includes a length and a width, and the distal portion of the unitary elongate body may be apportioned along its width to define the plurality of arms, each of the plurality of arms having a common thickness. In one embodiment, the unitary elongate body includes a length, a width and a thickness, and the distal portion of the unitary elongate body may be apportioned along its thickness to define the plurality of arms, each of the plurality of arms having a common width. In one embodiment, the proximal neck portion may be apportioned into a plurality of necks, and where the unitary elongate body may include a biased configuration where at least one arm may be adjacent to at least one neck. In various embodiments, a weight of the leaflet fixation device may be between 50-150 milligrams.

According to another aspect, a system includes a leaflet fixation device including a unitary elongate body including a proximal neck portion including a first tissue engaging surface and a distal portion including an arm having a second tissue engaging surface. The arm includes an open configuration where the first tissue engaging surface may be spaced away from the second tissue engaging surface, the arm being biased towards a closed configuration where the second tissue engaging surface may be retained adjacent to the first tissue engaging surface by a bias force. The system also includes a delivery tool including, for each arm, a spreader mechanism configured to independently translate the arm between the closed configuration and the open configuration.

In one embodiment the arm may be one of a plurality of arms biased towards the closed configuration, and in the closed configuration each arm of the unitary elongate body may be adjacent to a different part of the proximal neck portion of the unitary elongate body. In some embodiments, the proximal neck portion of the unitary elongate body, the distal portion of the unitary elongate body, or both may include a tissue retention feature including a barb, a hook, a tooth, a tine, a pore, a texture or a combination thereof. In one embodiment, the spreader mechanism may include a jaw, pivotably coupled to a distal end of the delivery tool, the jaw including a coupler configured to releasably couple the arm to the jaw, where rotation of the jaw in a first direction pulls the arm of the leaflet fixation device away from the proximal neck portion of the leaflet fixation device to the open configuration to provide a space therebetween configured for valvular tissue and where rotation of the jaw in a second direction returns the arm to the closed configuration. In one embodiment, each spreader mechanism includes a spreader arm, rotatably coupled to a distal end of the delivery tool, the spreader arm disposed to push the arm of the leaflet fixation device away from the proximal neck portion of the leaflet fixation device to the open configuration when rotated in a first direction to provide a space therebetween configured for valvular tissue, where rotation of the spreader arm in a second direction returns the arm to the closed configuration. In one embodiment, the proximal neck portion, the arm of the distal portion, or both of the leaflet fixation device include a tissue retention feature and the spreader mechanism may be configured to independently translate the arm between the closed configuration and the open configuration and to inhibit engagement between a tissue engagement feature and tissue during placement of the leaflet fixation device.

According to a further aspect, a method of joining leaflets of a cardiac valve includes the steps of advancing a delivery tool carrying a fixation device at its distal end towards a valve treatments site, the fixation device including a unitary elongate body including a proximal neck portion and a distal portion including an arm, where the arm includes an open configuration where the proximal neck portion of the unitary elongate body may be spaced away from the arm and a closed configuration where the arm may be retained adjacent to the proximal neck portion of the unitary elongate body by a bias force, and where the arm may be biased in the closed configuration at rest. The method includes positioning the delivery tool proximate to a first valve leaflet, actuating a spreader mechanism of the delivery tool to angularly displace the arm away from the proximal neck portion of the unitary elongate body into the open configuration, positioning the proximal neck portion of the unitary elongate body and the arm on opposing sides of the first valve leaflet and actuating the spreader mechanism to restore the arm to the closed configuration.

In some embodiments, the arm may be a first arm of a pair of arms biased towards the closed configuration, and the method may include the steps of positioning the delivery tool proximate to a second valve leaflet, actuating the spreader mechanism of the delivery tool to angularly displace a second arm away from the proximal neck portion of the unitary elongate body into the open configuration, positioning the proximal neck portion of the unitary elongate body and the second arm on opposing sides of the second valve leaflet and actuating the spreader mechanism to restore the second arm to the closed configuration.

With such an arrangement, a unitary, lightweight leaflet clip is provided for use in securing valve leaflets for cardia repair procedures. Using a unitary body to form the leaflet clip reduces the number and type of components involved in the leaflet clipping solution, thereby reducing the overall weight of the fixation device and failure risks associated with chronic interaction between components.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical illustrated component is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 2A-2D are perspective views of one embodiment of a valve fixation device disclosed herein;

FIGS. 3A-3C are perspective views of one embodiment of a valve fixation device disclosed herein;

DETAILED DESCRIPTION

Figure 1A:
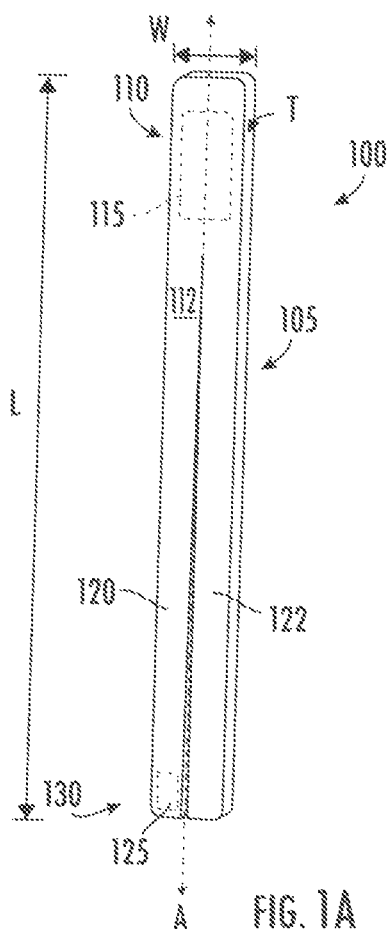
FIGS. 1A-1D are perspective views of one embodiment of a valve fixation device disclosed herein.

The present disclosure provides methods and devices for grasping and securing tissues such as valve leaflets to treat cardiac valve regurgitation. In one embodiment, a valve fixation device may comprise a unitary elongate member comprising at least one neck portion and at least one arm portion, the elongate member being biased towards a closed configuration wherein at least a pair of tissue engaging surfaces of the elongate member (for example, a tissue engaging surface on the neck portion and a tissue engaging surface of the arm portion) are held adjacent to each other by a bias force. The bias force is at least equal to a valve leaflet grasping force, enabling the fixation device to grasp and retain leaflets as part of cardiac treatment. A delivery tool including a spreader may independently translate the tissue engaging surfaces to enable cardiac leaflets to be captured and retained by and/or between the tissue engaging surfaces. The valve fixation device may include at least two arms, each of which may be independently controlled to grasp and capture opposing leaflets of a valve, such as the anterior and posterior leaflets of a mitral valve, to reduce the size of the valve opening and improve cardiac performance. In some embodiments, at least a portion of the fixation device includes one or more tissue retention mechanisms, including but not limited to teeth, barbs, hooks, tines, pores, or surface texture, etc., that improves fixation device retention. In some embodiments, the delivery tool may include one or more features, such as a shield or a standoff, configured to reduce interaction between tissue retention mechanisms and tissue during positioning of the fixation device.

These and other beneficial aspects of an implant and method of deployment are described in more detail below. Although embodiments of the present disclosure may be described with specific reference to mitral valves, the principles disclosed herein may be readily adapted to facilitate reconstruction of any valve annulus, for example including a tricuspid valve annulus and/or may similarly benefit any other dilatation, valve incompetency, valve leakage and other similar heart failure conditions.

As used herein, the term "distal" refers to the end farthest away from the medical professional when introducing a medical device into a patient, while the term "proximal" refers to the end closest to the medical professional when introducing a medical device into a patient.

FIGS. 1A-1D illustrate perspective views of one embodiment of a fixation device 100 that may be used as disclosed herein to reduce the size of a valve, for example by joining together valve leaflets. The fixation device 100 is shown formed of a unitary, elongate body 105 having a proximal neck portion 110 and a distal portion 130 comprising one or more arms of the elongate body. In various embodiments, the body 105 may be manufactured from a shape memory alloy (SMA) or similar materials with the ability to recover a pre-defined configuration. Such materials include, but are not limited to, Nickel Titanium, Graphene, Nitinol, copper-aluminum-nickel and the like.

Such materials are referred to herein as biased towards the pre-defined configuration. A bias force is the recovery force of the shaped memory alloy, e.g., the force exhibited by the body to recover (e.g. return to its pre-defined configuration) under the strain of deformation from the pre-defined configuration. The bias force is a function of the size, shape, and composition of shaped material. In one example embodiment, the overall elongate body may have a length of 14 mm-24 mm, to provide a "folded" length between 7 mm and 12 mm, a width of 2 mm-6 mm and a thickness of 0.25-0.75 mm, providing a device having a grasping force of between 0.1 and 0.5 lbs. Although a fixation device having ranges of length, width, and/or thickness is disclosed, it is appreciated that one of skill in the art may develop similar fixation devices capable of providing similar bias or grasping forces that urge the fixation device towards a closed, tissue retaining configuration, and such similar devices are considered to be within the scope of this disclosure.

According to one aspect, the fixation device may be manufactured to provide sufficient grasping force to enable it to fixedly attach to leaflet tissue without imparting undue gravitational forces that may disrupt remaining valve function. In this way, the fixation device has a mass that is not significantly larger than necessary such that the weight of the fixation device does not negatively impact the leaflet or nearby tissue. For example, a device 100 may weigh between 50-150 mg, for example 65 mg, or the like, e.g., such that a weight of a clamp may not undesirably interfere with leaflet operation.

FIG. 1A illustrates the unitary elongate body 105 in an unbiased state. In one embodiment, the unitary elongate body 105 has a length L that extends longitudinally along an axis A, a width W, perpendicular to the Axis A, and a thickness T. In some embodiments, such as that shown in FIG. 1A, the width is fixed along the length L. In other embodiments, the width may vary (increase, decrease) along the length L. Similarly, although the thickness T is shown to be relatively uniform along the length and width, it is appreciated that in various embodiments the thickness may vary (increase, decrease) along the length L or across the width W. In the embodiment of FIG. 1A, as will be described in more detail below, the distal portion 130 of the unitary elongate body 105 is shown apportioned across its width into a plurality of arms, such as arm 120 and arm 122.

Figure 1B:
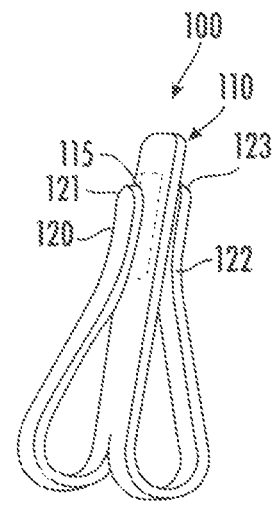
Figure 1C:
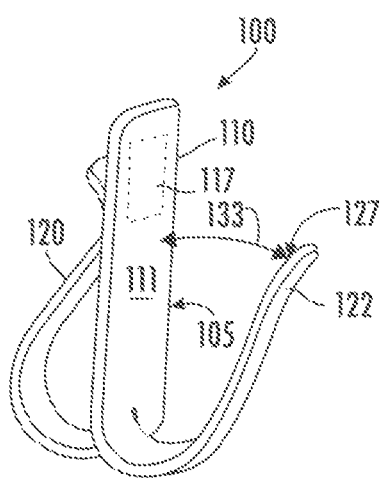

The unitary elongate body has several surfaces, including a forward surface 112, shown in FIG. 1A, and a rear surface 111 (shown in FIG. 1C). At least a portion of the proximal neck portion 110 of the unitary elongate body 105 includes a tissue engaging portion 115, and at least a portion of a distal end of an arm, such as arm 120, also includes a tissue engaging surface portion 125. Although certain portions of the body 105 are designated as tissue engaging surfaces, it is appreciated that the tissue engaging surface portion may include a larger or smaller area than that designated, and that the tissue engaging portion may be any surface of the body 105 that contacts leaflet tissue during use.

According to one embodiment, the pre-defined configuration of the unitary elongate body comprises a closed configuration wherein common surfaces of proximal and distal portions of the unitary elongate body are positioned close to and opposing each other to form a leaflet fixation device.

For example, FIG. 1B illustrates the unitary elongate body 100 in its biased, closed, configuration. Each arm, 120, 122 is differently biased, formed such that distal ends 121, 123 of the respective arms 120, 122 contact different surfaces (e.g., 111, 112) of the proximal neck portion 110 of the leaflet fixation device 100. For example, distal end 121 of arm 120 contacts the proximal neck portion 110 of the device 100 at a tissue engagement surface 115, while the distal end 123 of arm 122 contacts the proximal neck portion 110 of the device 100 on the opposing surface. As a result, the fixation device 100 leverages the resistive forces of shape memory materials to provide a unitary, low profile, light weight retention mechanism for valve leaflet treatment.

FIG. 1C illustrates the rearward facing surface 111 of the fixation device 100 comprising biased arms 120, 122 and shown including tissue engaging surface 117 on its proximal end 110. The embodiment of the fixation device 100 of FIGS. 1A-1D comprises a two-armed retention device, wherein each of the arms are biased towards an opposing surface of the proximal neck portion of the body 105. Thus, a distal tissue engaging surface 127 of arm 122, in a biased configuration, contacts or is otherwise close to and facing a tissue engaging surface 117. In FIG. 1C, the arm 122 is shown pulled away from the proximal neck portion 110 of body 105 by an angular extent 133. The angular extent 133 corresponds to an open configuration of the arm 122, that leaving a gap between the body 105 and the arm 122 that is sufficiently wide to enable leaflet tissue to be disposed therebetween. In some embodiments, the angular extent 133 may range between 75 and 120 degrees or more, for example, to leave a gap in the range of 90 degrees.

Figure 1D:
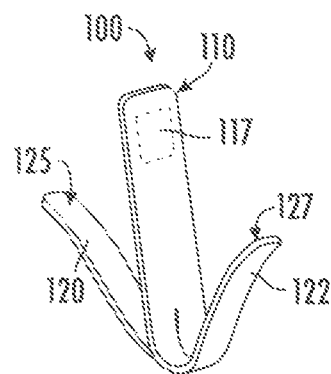

FIG. 1D is a diagram illustrating the fixation device 100 in a fully open configuration, with both arms 120, 122 spaced apart from the proximal neck portion 110 such that the distal tissue engaging surfaces 125, 127 are spaced apart from the proximal tissue engaging surfaces 117. As described in more detail below, according to one aspect, each of the arms 120, 122 of the fixation device 100 may be independently opened and closed, enabling greater precision and accuracy when grabbing tissue by enabling grasping of individual leaflets during the procedure.

In the embodiment of FIGS. 1A-1D, where the arms of the distal portion of the unitary elongate body are formed by apportioning the width of the distal portion into segments, the distal tissue engaging surface (125, 127) comprises only approximately half (or other portion, when arms have different widths) of the width W of the unitary body 105. In such a configuration, the grasping force of each arm should be selected to compensate for the reduced size of the tissue engaging surface.

FIGS. 2A-2D illustrate various views of a second embodiment of a fixation device 200 comprising a unitary elongate body 205 having a length L, a width W, and a thickness T which may correspond generally in L and W dimension to the device 100 of FIGS. 1A-1D, and may range in thickness T from the same dimension to double the thickness or more at least partially along its length, as will be described. In FIG. 2A, the unitary elongate body 205 is shown in an unbiased configuration. The body 205 includes a proximal neck portion 210 and a distal portion 230, the proximal neck portion 210 comprising a tissue engaging surface 215 and the distal portion 230 comprising a tissue engaging surface 225. In some embodiments, the thickness of the distal portion 230 may be greater than the thickness of the proximal neck portion 210, although the disclosure is not so limited. Arms 220, 222 of the fixation device 200 may be formed by apportioning the thickness T of the distal portion into segments. With such an arrangement, the tissue engaging surface area 225 of the distal end 230 of the fixation device 200 utilizes the entire width W of the body 205, enabling a more comprehensive use of the proximal tissue engaging portion 215 for securing tissue. In some embodiments, increasing the tissue engaging surface area in this manner may enable lighter weight materials to be used for a fixation device capable of achieving the desired bias force for leaflet grasping.

FIG. 2B is a side view of the fixation device 200. The distal portion 230 of the device 200 is shown bisected along its thickness T, forming two arms 220, 222 which are biased towards a closed configuration wherein the distal ends of arms 220, 222 contact, or are otherwise close to and facing opposing surfaces of the proximal neck portion 210 of the device 200.

FIG. 2C illustrates the device 200 in a partially open configuration, wherein the arm 220 has been pulled or pushed back from the biased, closed configuration to expose distal tissue engaging surface 227 and proximal tissue engaging surface 217 (not visible) to leaflet tissue.

FIG. 2D illustrates the device 200 in a fully open configuration, wherein both arms 220, 222 have been pushed or pulled away from their biased, closed configuration to an open configuration wherein gaps G1, G2 enable leaflet tissue to be disposed between tissue engaging surfaces of the device 200 for capture.

FIGS. 3A-3C illustrate an alternate embodiment of a fixation device 300. Like the device 200 of FIGS. 2A-2C, the device of FIGS. 3A-3C includes arms 320, 322 formed by bisecting the distal portion of the elongate body 305 along its thickness. The arms 320, 322 are biased towards a closed configuration, wherein distal portions of the arms 320, 322 contact, or are close to and facing the proximal neck portion 310 of the body 305. In the embodiment of FIGS. 3A, 3C, the proximal neck portion 310 of the body 305 includes one or more tissue retention features, such as tissue retention feature 323. In FIGS. 3A-3C, the tissue retention features 323 are shown disposed upon opposing surfaces 311, 312 the proximal neck portion 310 of the elongate body 305. The illustrated tissue retention features 323 comprise a tooth that extends at an angle from a longitudinal axis A of the elongate body. In one embodiment, the tooth is distally angled, to secure leaflet tissue, when disposed between the arms 320, 322 and the proximal tissue engaging surfaces, against pullout due to chronic palpatory forces.

In some embodiments, the one or more tissue retention mechanisms may be arranged in columns extending along at least one of the plurality of arms such that the plurality of retention mechanisms are in different planes. The protrusions may extend not more than 50% through a thickness of a wall of the leaflet, e.g., the protrusions may not extend into the wall of a leaflet and may instead distort the tissue. The protrusions may extend a distance from an arm that may be about 0.5 millimeters to about 1.5 millimeters.

FIG. 3B is a cross-sectional view of device 300, illustrating tissue retention mechanisms 323 deployed on opposing surfaces 311, 312 of the proximal end 310 of the device 300. As shown in FIG. 3B, as the arms 320, 322 are urged towards their biased configuration, the arms will push any captured tissue towards the tissue retention mechanisms 323, improving the affixation of the device 300 to leaflet tissue. FIG. 3C illustrates the device 300 in a fully open configuration, providing gaps G1, G2 between the proximal end 310 of the device 300 and respective arms 320, 322. It is appreciated that, when employing tissue retention mechanisms such as teeth 323, the resiliency of the unitary elongate body may be selected to ensure that the gaps G1, G2 are wide enough to accommodate leaflet tissue without interference from the retention mechanisms 323. In other words, the open configuration should provide a gap at least equal to expected leaflet tissue thickness plus the protrusion extent of any tissue retention mechanism used to retain the leaflet.

Although FIGS. 3A-3C illustrate tissue retention mechanisms relatively equally disposed on opposing surfaces of the proximal neck portion 310 of the body 305, it is appreciated that tissue retention mechanisms may take many forms and may be deployed in various patterns which are optimized to the particular tissue to be captured by the fixation device, as well as to secure the device against chronic palpatory forces that act upon it. Thus, although a particularly shaped tooth is shown in FIGS. 3A-3C, the present disclosure is not limited to the use of teeth, but additionally encompasses barbs, hooks, tines, or another feature that may be used to engage or interact with leaflet tissue.

Figure 4:
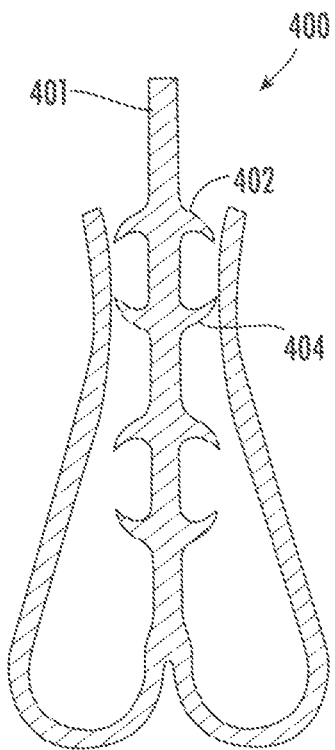
FIG. 4 illustrates one embodiment of a valve fixation device disclosed herein.

FIGS. 4-7 illustrate various embodiments of tissue retention devices that employ different tissue retention mechanisms. FIG. 4 is a cross section view of one embodiment of a device 400 that includes a plurality of tissue retention mechanisms disposed on the proximal neck portion 401 of the device 400, including distally facing teeth 402 and proximally facing teeth 404. Such embodiments may improve the ability of tissue to be grasped between the proximally and distally facing teeth, to assist in retaining leaflet tissue by the device 400.

Figure 5:
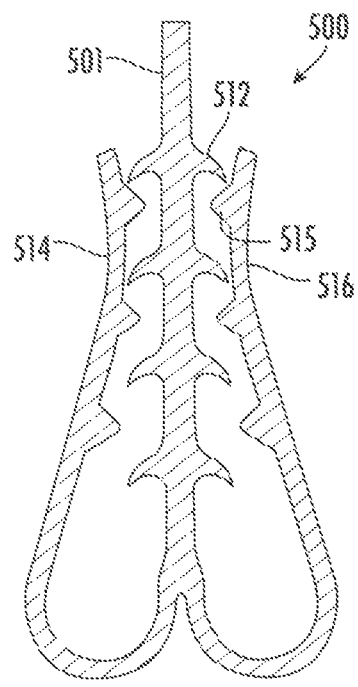
FIG. 5 illustrates one embodiment of a valve fixation device disclosed herein.

FIG. 5 is a cross section view of an embodiment of a device 500 that includes a plurality of tissue retention mechanisms, wherein some tissue retention mechanisms, such as neck teeth 512, are disposed on the proximal neck portion 501 of the device 500, and other tissue retention mechanisms, such as tissue engaging teeth 515, are disposed on the arms 514, 516. With such an arrangement, tissue retention is applied to both sides of a captured leaflet, further increasing the strength of affixation of the device 500 to the leaflet.

Figure 6:
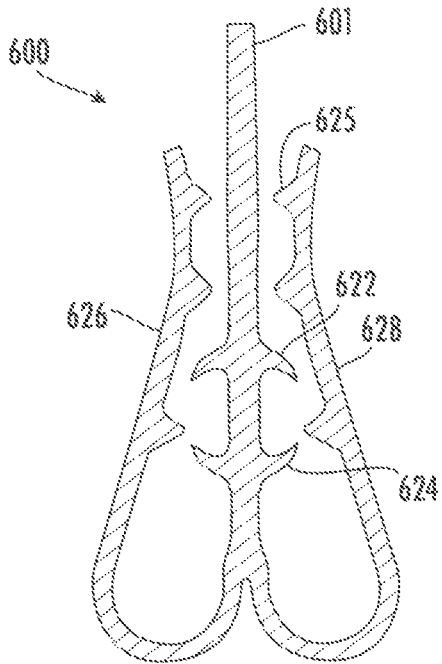
FIG. 6 illustrates one embodiment of a valve fixation device disclosed herein.

FIG. 6 is a cross section view of an embodiment of a device 600 that includes a plurality of tissue retention mechanisms, wherein some tissue retention mechanisms, such as neck teeth 622, 624, are disposed on the proximal neck portion 601 of the device 600, and other tissue retention mechanisms, such as tissue engaging teeth 625, are disposed on the arms 626, 628. The embodiment of FIG. 6 illustrates how the pattern of tissue retention mechanisms may vary in accordance with the particular tissue or chronic use conditions of the clip.

Figure 7:
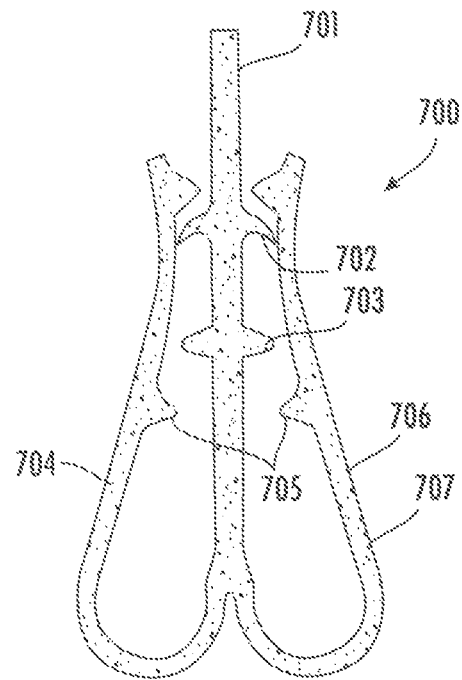
FIG. 7 illustrates one embodiment of a valve fixation device disclosed herein.

FIG. 7 is a side view perspective of an embodiment of a device 700 that includes a plurality of tissue retention mechanisms, including both tissue retention mechanisms that are configured to pierce tissue, such as neck teeth 702, 703 on proximal neck portion 701, and tissue engaging teeth 705 on arms 704, 706, as well as tissue retention mechanisms such as pores 707 which are configured to encourage endothelialization (e.g., tissue ingrowth) into the device 700. For example, the pore size may range from between 5 and 30 μm. The pores may be distributed over portion or all of the elongate body. Other methods of promoting tissue ingrowth along a portion of or the entire elongate body, for example by modifying the surface texture of the elongate body, coating the body with pro-angiogenic drugs, etc., are also within the scope of this disclosure.

Figure 8:
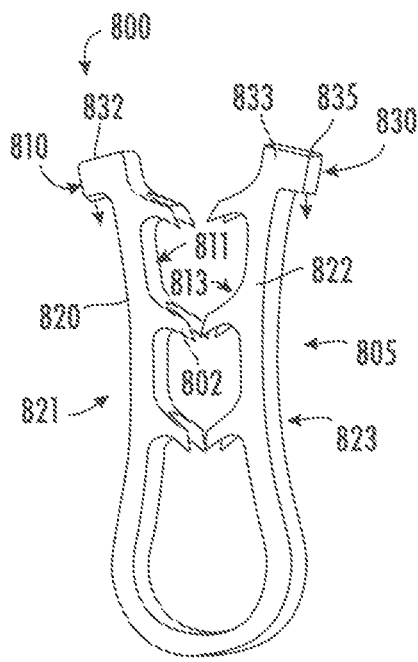
FIG. 8 illustrates one embodiment of a valve fixation device disclosed herein.
Figure 9:
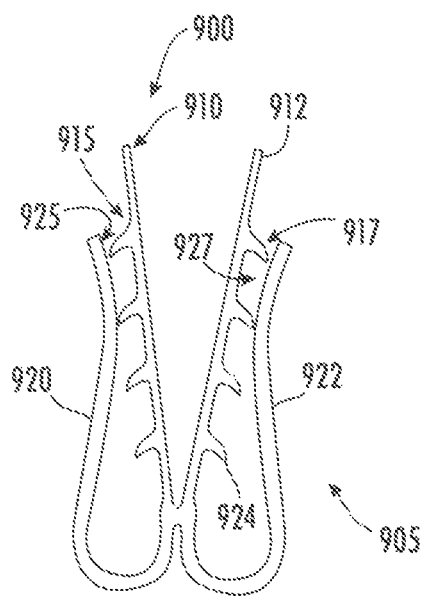
FIG. 9 illustrates one embodiment of a valve fixation device disclosed herein.
Figure 10:
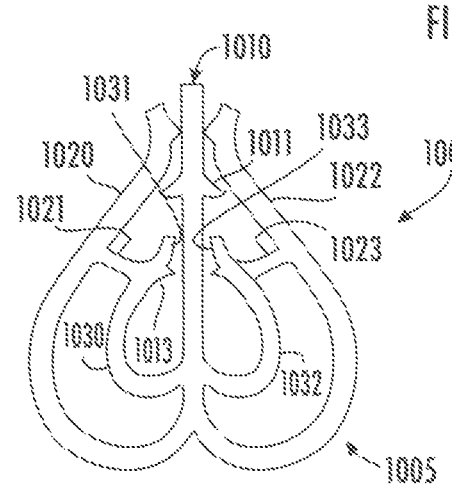
FIG. 10 illustrates one embodiment of a valve fixation device disclosed herein.

FIGS. 8-10 illustrate alternate embodiments of tissue fixation devices which may be formed from a resilient material that leverages the bias forces of a closed configuration to provide leaflet grasping forces for retaining the leaflet within the device.

FIG. 8 illustrates a fixation device 800 comprising an elongate body 805 formed into two opposing arms 820, 822, and bent so that the proximal end 810 of the elongate body faces the distal end 830 of the elongate body, and portions 821, 823 of the arms are biased to a closed configuration such that tissue engaging surfaces 811, 813 of the arms are adjacent to and face each other to enable tissue to be grasped between the arms 820, 822. Each arm 820, 822 is shown to include tissue retention mechanisms such as teeth 802 disposed in parallel columns along surfaces 811, 813 of the device 800. In the embodiment of FIG. 8, the proximal end 810 and distal end 830 of the elongate body 805 may each include a coupler 832, 833, that may be used, for example, to couple the device 800 to a delivery tool to manage delivery of the device 800 to the valve leaflet. As described in more detail below, in one embodiment, the coupler 832 may include a bore (not shown), having a central lumen 835 extending therethrough configured to accept a pin or other mechanism to releasably secure the arm to a delivery tool which is configured to move each arm 820, 822 independently from other arms of the body 805.

FIG. 9 is a side view of an embodiment of a fixation device 900 formed from a unitary elongate body 905 which has been apportioned along its thickness to form both proximal arms 910, 912 in the proximal neck portion of the elongate body 905 as well as distal arms 920, 922 in the distal portion of elongate body 905. In one embodiment, distal arm 920 includes a biased configuration wherein a distal tissue engaging surface 925 is adjacent to, and faces, a proximal tissue engaging surface 915 of the proximal arm 910. Distal arm 922 also includes a biased configuration wherein a distal tissue engaging surface 927 is adjacent to, and faces, a proximal tissue engaging surface 917 of the proximal arm 910. Such a fixation device may serve to dampen the strain upon the leaflets by allowing the fixation portions to move more freely with the valve during use, while providing force necessary to retain the leaflets in a joined configuration to treat disease. In the embodiment of FIG. 9, each proximal arm 910, 912 is shown to include tissue retention mechanisms, such as teeth 924, disposed along its length. As discussed with regard to FIGS. 4-7, additional or alternate tissue retention mechanisms and patterns may be substituted herein consistent with this disclosure.

FIG. 10 is a side view of an embodiment of a fixation device 1000 formed from a unitary elongate body 1005 which has been apportioned along its thickness to provide a plurality of distal arms 1020, 1022, 1030, 1032, each of which is biased to a closed configuration wherein at distal tissue engaging surfaces 1021, 1023, 1031, 1033 are oriented towards a tissue engaging surface of the proximal neck portion 1010 of the body 1050. In one embodiment, connectors 1021, 1023 may be deployed to couple interior distal arms 1030, 1032 to exterior distal arms 1020, 1022 so that, when the exterior distal arms 1020, 1022 are spread, the interior distal arms 1030, 1032 are pulled open, allowing tissue to be disposed between the arms 1020, 1030, 1022, 1032 an the proximal neck portion 1010 of the body 1050. As shown in FIG. 10, tissue retention mechanisms such as teeth 1011, 1013 may be strategically placed along the proximal neck portion 1010 and/or arms 1020, 1022, 1030, 1032 to secure tissue within the device 1000.

The leaflet retaining devices such as those described in various embodiments above, may be used in a variety of therapeutic procedures, including endovascular, minimally-invasive, and open surgical procedures, and can be used in various anatomical regions, including the abdomen, thorax, cardiovascular system, heart, intestinal tract, stomach, urinary tract, bladder, lung, and other organs, vessels, and tissues. The fixation devices may be particularly useful for procedures requiring minimally-invasive or endovascular access to remote tissue locations, where the instruments utilized must negotiate long, narrow, and tortuous pathways to the treatment site.

For example, the leaflet fixation device may be used for edge to edge repair of a cardiac valve including but not limited to a mitral valve. The mitral valve can be accessed from a remote surgical or vascular access point and the two valve leaflets may be brought together at a fixation point using the fixation device via endovascular or minimally invasive approaches. For example, the fixation device may be used to join the anterior leaflet and posterior leaflet of the mitral valve at any location of the leaflets between the anterolateral and posteromedial commissures of the valve. Multiple fixation devices may be used to couple the leaflets at various points of the valve. In some circumstances the fixation device may be used in open surgical approaches as well. According to the invention, the mitral valve may be approached either from the atrial side (antegrade approach) or the ventricular side (retrograde approach), and either through blood vessels or through the heart wall.

The fixation device may be delivered using a tool that is positioned near a desired treatment site and used to manipulate the fixation device, enabling the device to grasp the target tissue. In endovascular applications, the delivery tool may typically be a working catheter that is translated to the treatment site via a delivery catheter/guidewire system. In surgical applications, the delivery tool may typically a surgical instrument.

In one embodiment, the method includes the steps of advancing the delivery tool having a proximal end and a distal end to a location within a patient's body, wherein the delivery tool releasably carries the fixation device and is configured to translate the fixation device between its open and closed configuration to grasp leaflet tissue, and to release the leaflet tissue following positioning of the fixation device on the leaflets.

FIGS. 11A-11E illustrate features of one embodiment of a delivery tool 1100 which may be used to deliver a fixation device 1150 to a treatment site. The delivery tool 1100 is shown to include a support arm 1120 comprising a proximal end 1101 and distal end 1103, the distal end 1103 having an opening defining a sleeve configured to releasably accept the proximal neck portion 1110 of the fixation device 1150. In some embodiments, for example, the proximal neck portion 1110 of the fixation device may include a slot which cooperates with a tab (not shown) internal to the sleeve to retain the proximal neck portion 1110 of the device within the sleeve during deployment. Following deployment, the tab may be withdrawn from the slot, freeing the device from the delivery tool.

The delivery tool 1100 further includes one or more spreader mechanisms, such as jaws 1152, 1154. Each jaw 1152, 1154 is generally matched in shape to the curve of the fixation device 1150 to minimize the profile of the delivery tool. In one embodiment, the jaws 1152, 1154 comprise a curved shape to minimize the potential for interference between the distal end 1103 of the delivery tool and cardiac features, such as chordae tendinea and the like. In one embodiment, each jaw 1152, 1154 is pivotably mounted at pivot point 1156 of its distal end to the distal end 1103 of the support arm 1120 of the delivery tool 1100. Guide cables 1122, 1124 may extend from the proximal end of the jaw to the distal end 1103 of the support arm 1120 of the delivery tool 1100, wherein actuation of the drive cables, for example, for example, pulling the cables proximally through the sleeve, may pull the jaws 1152, 1154 away from a longitudinal axis defined by the delivery tool. In one embodiment, the distal arms of the fixation device 1150 are releasably coupled to the proximal ends of the jaws 1152, 1154 such that when the jaw is pulled away from the longitudinal axis of the delivery tool, the distal arm is also pulled away, creating a gap which may be used to grasp leaflet tissue.

Figure 11A:
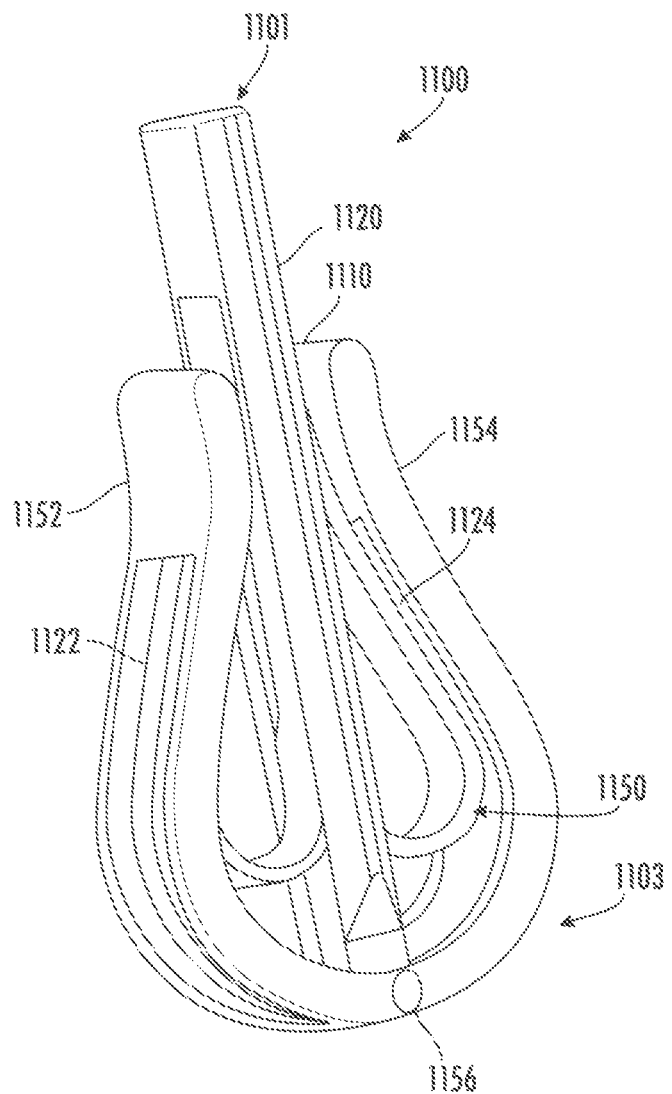
FIGS. 11A-11F illustrate various configurations and features of embodiments of a delivery mechanism for use in delivering the valve fixation devices disclosed in various embodiments herein, to a valve treatment site.
Figure 11B:
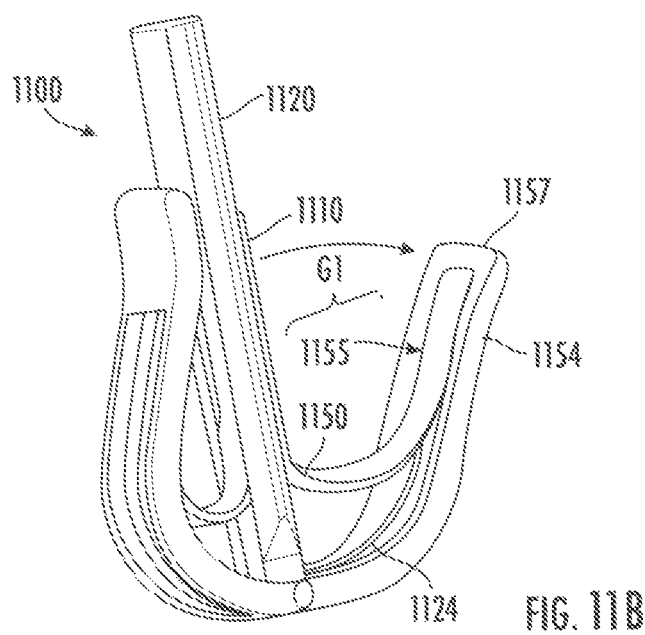

For example, FIG. 11B illustrates the delivery tool 1100 supporting the fixation device 1150 in a partially open configuration, wherein the jaw 1154 is releasably coupled at its proximal end 1157 to the distal arm 1155 of the fixation device 1150. Guide cable 1124 may be pulled into the support arm 1120 to open the jaw 1154 to create a gap G1 for accepting leaflet tissue. The guide cable 1124 may then be released or otherwise actuated to allow the arm 1155 to return to its biased, closed configuration to capture leaflet tissue between the arm 1155 and the proximal neck portion 1110 of the fixation device 1150.

Figure 11C:
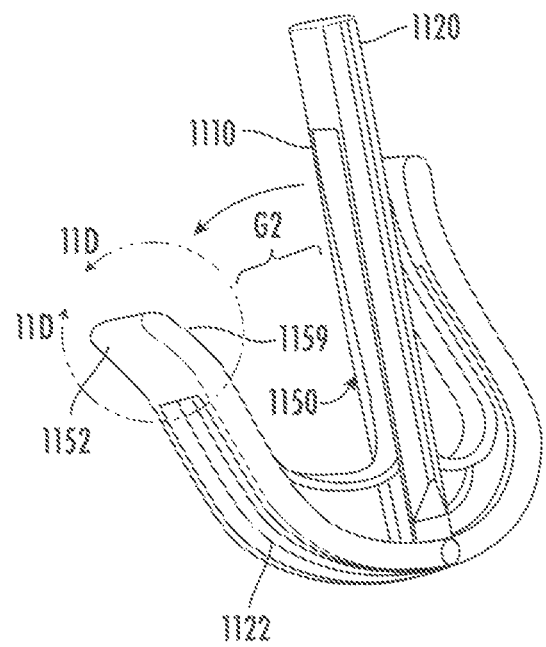

FIG. 11C illustrates the actuation of the second jaw 1152, for example which may occur by manipulation of the guide cable 1122 through the support arm 1120 as described above. When the guide cable 1122 is pulled proximally through the support arm 1120, the jaw 1152 opens. The distal arm 1159, which is releasably coupled to the jaw 1152, also is pulled away from the proximal neck portion 1110 of the fixation device 1150 by action of the jaw, generating a gap G2 for capturing a second valve leaflet. Once the valve leaflet is positioned within the gap G2, the guide cable 1122 may be released or otherwise controlled to allow the distal arm 1159 to return to its biased configuration, capturing tissue between the arm 1159 and the proximal neck portion 1110 of the device 1150.

Figure 11D:
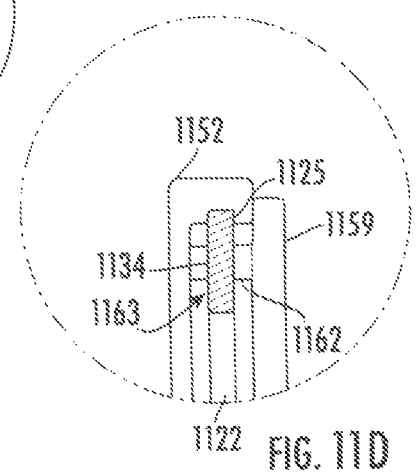

FIG. 11D is a close-up cross section of an example of a system for coupling the distal arm 1159 to the jaw 1152. In one embodiment, as described above, the distal arm may have a coupler 1162 disposed at its distal end. The coupler may comprise, for example, a protuberance having a bore 1163 extending therethrough, with the bore sized to accept a distal end of the guide cable 1122. In some embodiments, the guide cable 1122 may include a drive tube having a threaded coupler 1134 disposed on its distal end 1125. The threads of the coupler may interact with threads or other features on the internal surface of the bore 1163 to secure the threaded coupler 1134 within the bore 1163. In some embodiments, the drive tube may be rotatable, and rotation of the drive tube may translate the drive tube axially within the bore 1163. Once the fixation device has been manipulated to grasp both anterior and posterior leaflets, actuation of the drive to may be performed to distally translate the drive tube out through bore 1163, releasing the coupling between the arm 1159 of the fixation device and jaw 1152 of the delivery tool, and enabling removal of the delivery tool from the treatment site.

Figure 11E:
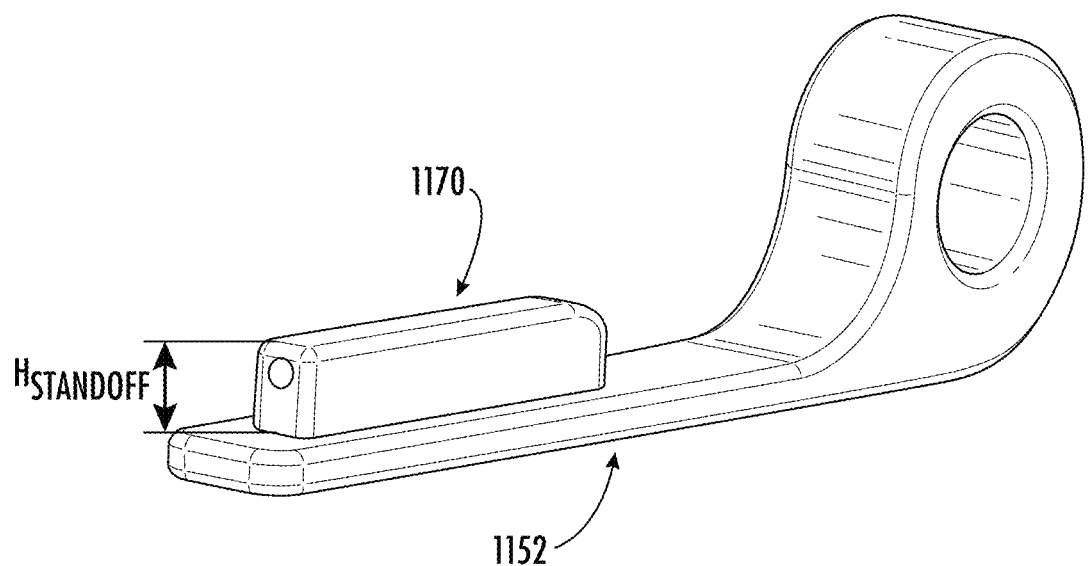

In some embodiments, the connection between the delivery tool and the fixation device may be formed to inhibit affixation of the fixation device during its placement, to facilitating positioning of the fixation device on the leaflets without tissue interference. For example, FIG. 11E is a close up view of one embodiment of a jaw 1152 of a delivery tool, including a sleeve 1170 disposed longitudinally along at least a portion of the length of the jaw. The sleeve 1170, in one embodiment, provides a standoff which maintains a space between the tissue retention mechanisms and an opposing tissue engagement surface, to inhibit entry of the tissue retention mechanisms into tissue during positioning of the fixation device. A height $H_{STANDOFF}$ of the sleeve 1170 may generally correspond to the protrusion distance of any tissue retention mechanism of a fixation device.

Figure 11F:
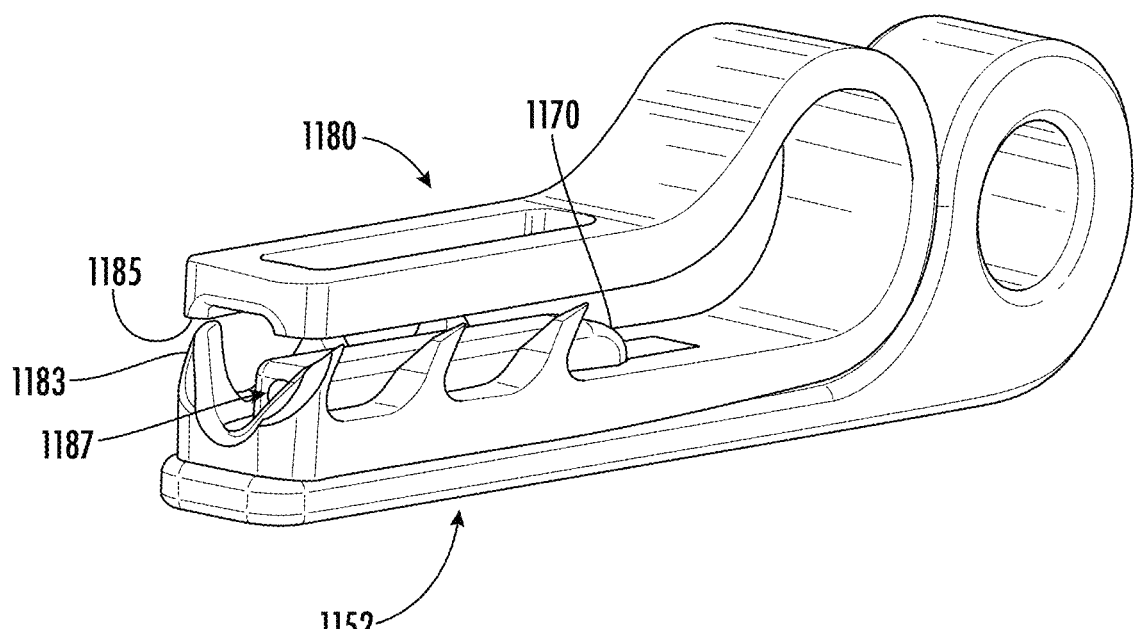

FIG. 11F, for example, illustrates a fixation device 1180 disposed upon the jaw portion 1152 of a delivery system. The fixation device 1180 is shown to include tissue retention features (e.g., teeth) 1183 disposed along edges of the device 1180 and oriented and protruding towards a tissue engaging surface 1185 of the fixation device 1180. The sleeve 1170 is configured to at least partially inhibit entry of the teeth 1183. For example, the sleeve may have a height that is equal to at least half of the extent of protrusion of the teeth 1183. In some embodiments, the sleeve 1170 may include a bore 1187 extending therethrough, for example, to slidably accept a cable (not shown) that opens and closes the jaw of the delivery tool. It should be noted that, although a unitary sleeve is shown in FIGS. 11E and 11F, alternative methods of inhibiting tissue affixation during placement of the fixation device, including but not limited to separate spacers disposed along the length of the jaw, shields disposed over the tissue retention mechanisms and the like are considered to be within the scope of this disclosure.

Figure 12A:
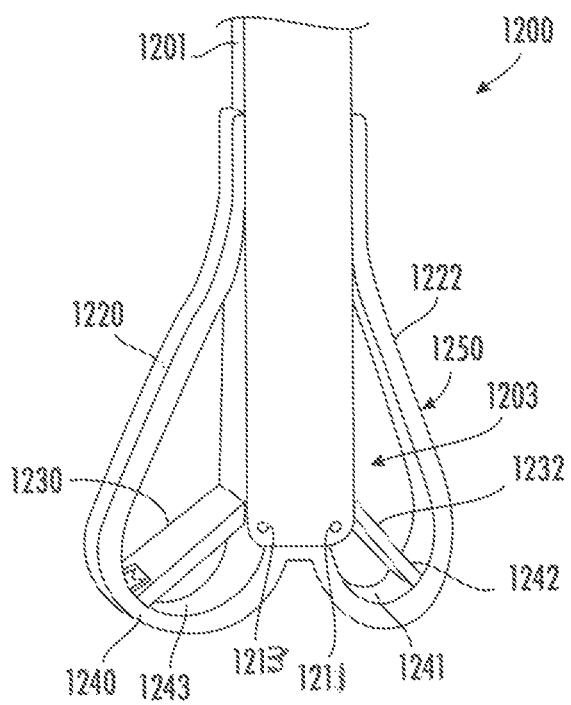
FIGS. 12A-12C illustrate various configurations of one embodiment of a delivery mechanism for use in delivering the valve fixation devices disclosed in various embodiments herein, to a valve treatment site.
Figure 12B:
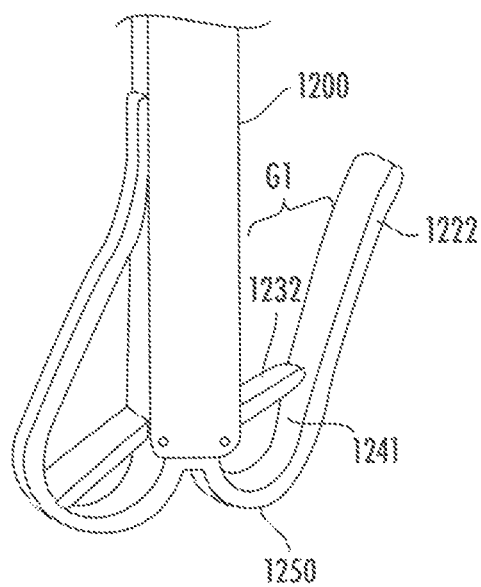
Figure 12C:
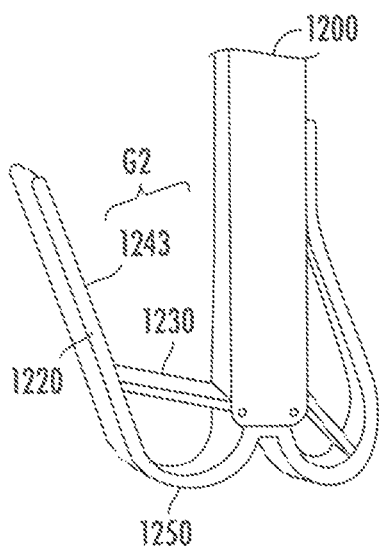

FIGS. 12A-12C illustrate an alternate embodiment of a delivery tool 1200 that may be used to deliver a fixation device 1250 such as those described herein in various embodiments, to a treatment site. The delivery tool includes a proximal end 1201 and a distal end 1203, and a pair of spreader arms 1230, 1232 rotatably disposed on the distal end 1203 of the delivery tool, wherein the spreader arms are operable to push the distal arms 1220, 1222 of the fixation device 1250 away from a longitudinal axis defined by the delivery tool to thereby generate a gap between the tool 1200 and the arms 1220, 1222 for corralling leaflet tissue. In some embodiments, the delivery tool may include a distal sleeve, configured to releasably carry the proximal neck portion 1201 of the fixation device to the treatment site. In various embodiments, each spreader arm may be rotatably coupled to the proximal end 1201 of the delivery tool, for example at pivot points 1211, 1213, and adapted to move smoothly over an internal surface 1241, 1243 of the arms 1220, 1222. For example, in one embodiment, each spreader arm 1230, 1232 may include a roller 1240, 1242 disposed on its distal end that enables the spreader arm to smoothly glide over the surfaces 1241, 1243 while providing a pushing force that acts against the biased configuration of the arms to generate the gap. It can be appreciated that the length of each spreader arm may vary depending upon the particular architecture of the fixation device but should be sufficient to allow the spreader arm to generate a gap that is capable of accepting leaflet tissue when rotated about its pivot point.

For example, referring now to FIG. 12B, the delivery device is shown in a partially open position, wherein the spreader arm 1232 has been rotated across the surface 1241 of the distal arm 1222 to a position generally perpendicular to the axis of the delivery device. The rotation force of the spreader arm is sufficient to counteract the bias forces of the fixation device 1250, causing the distal arm 1222 to be pushed away from the delivery tool 1200 and generating a gap G1 between the tool 1200 and the distal arm 1222 for accepting tissue. When tissue has been corralled between the tool 1200 and the distal arm 1222, the spreader arm 1232 may be rotated distally, removing the counteracting forces and allowing the distal arm 1222 to return to its biased configuration to capture tissue between the tool 1200 and the distal arm 1222.

FIG. 12C illustrates the delivery device in a partially open position, wherein the spreader arm 1230 has been rotated across the surface 1243 of the distal arm 1220 to a position generally perpendicular to the axis of the delivery tool 1200. The rotation force of the spreader arm 1230 is sufficient to counteract the bias forces of the fixation device 1250, causing the distal arm 1220 to be pushed away from the delivery tool 1200 and generating a gap G2 between the tool 1200 and the distal arm 1220 for accepting tissue. When tissue has been corralled between the tool 1200 and the distal arm 1220, the spreader arm 1230 may be rotated distally, removing the counteracting forces and allowing the distal arm 1220 to return to its biased configuration to capture tissue between the tool 1200 and the distal arm 1220.

Once both leaflets are secured, the delivery tool may be removed, for example by releasing or otherwise expelling the proximal end of the fixation device 1250 from the delivery tool 1200.

FIGS. 13A-13D illustrate various structures of a heart 1300, including a mitral valve 1320 comprising posterior and anterior leaflets 1322, 1324 supported by chordae tendinea 1325 which are controlled by papillary muscles 1326. In the illustrated embodiment, a delivery catheter 1400 supports a delivery tool 1450 and may be used to navigate the delivery tool 1450 to a treatment site, for example below a mitral annulus 1340.

Figure 13A:
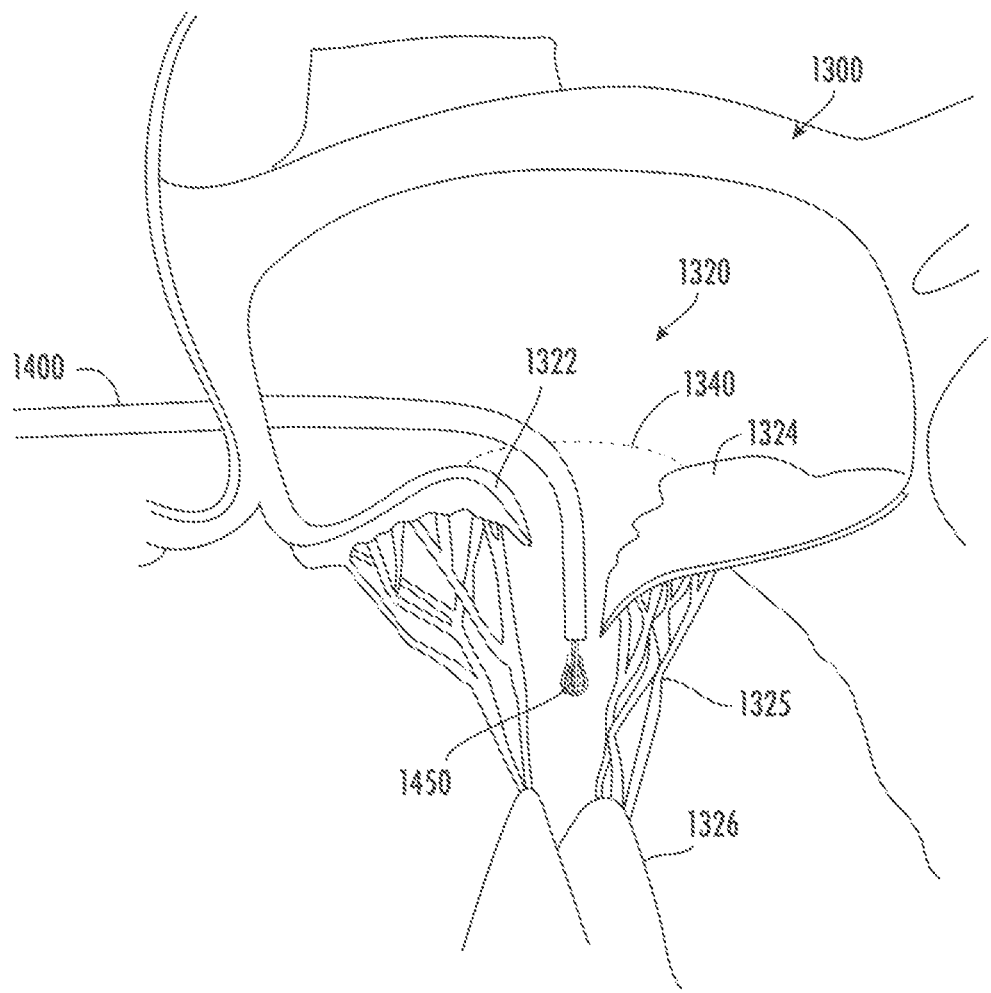
FIGS. 13A-13D illustrate examples of steps that may be performed for treatment of a heart valve using the valve fixation devices disclosed in various embodiments herein.
Figure 13B:
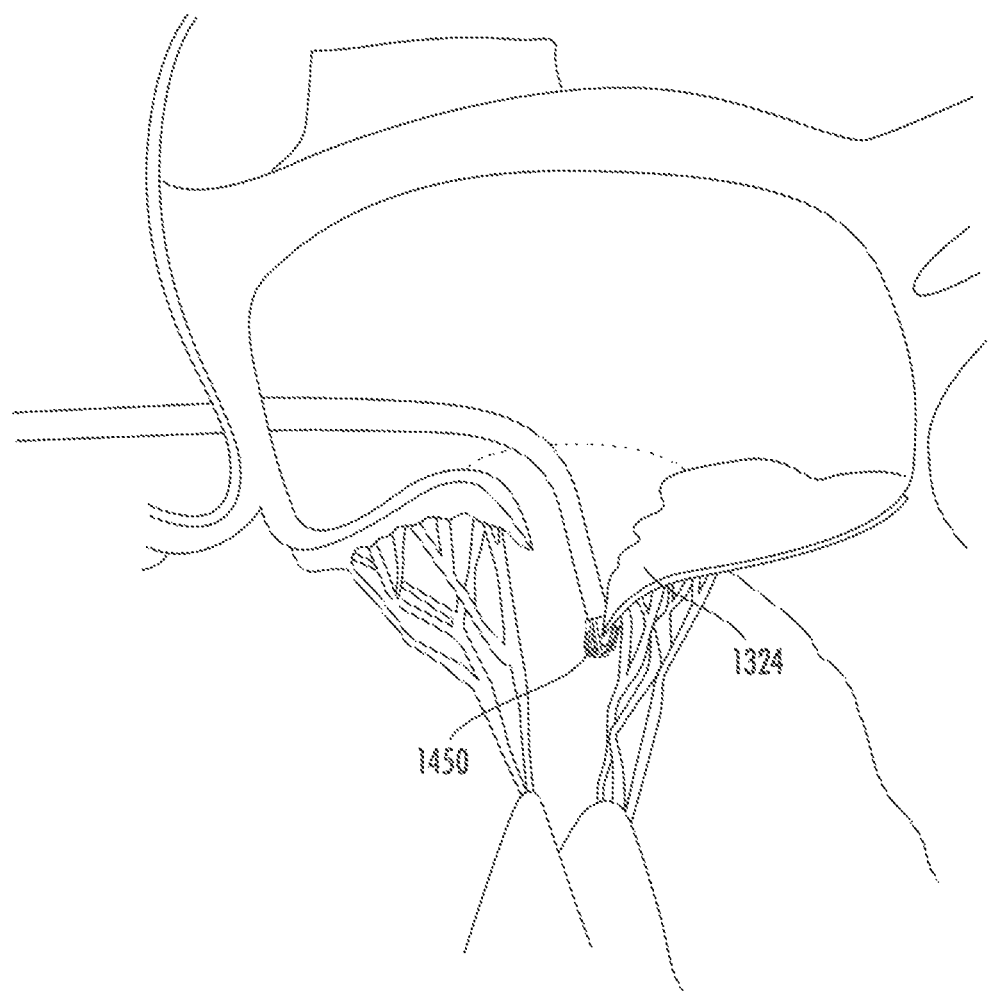
Figure 13C:
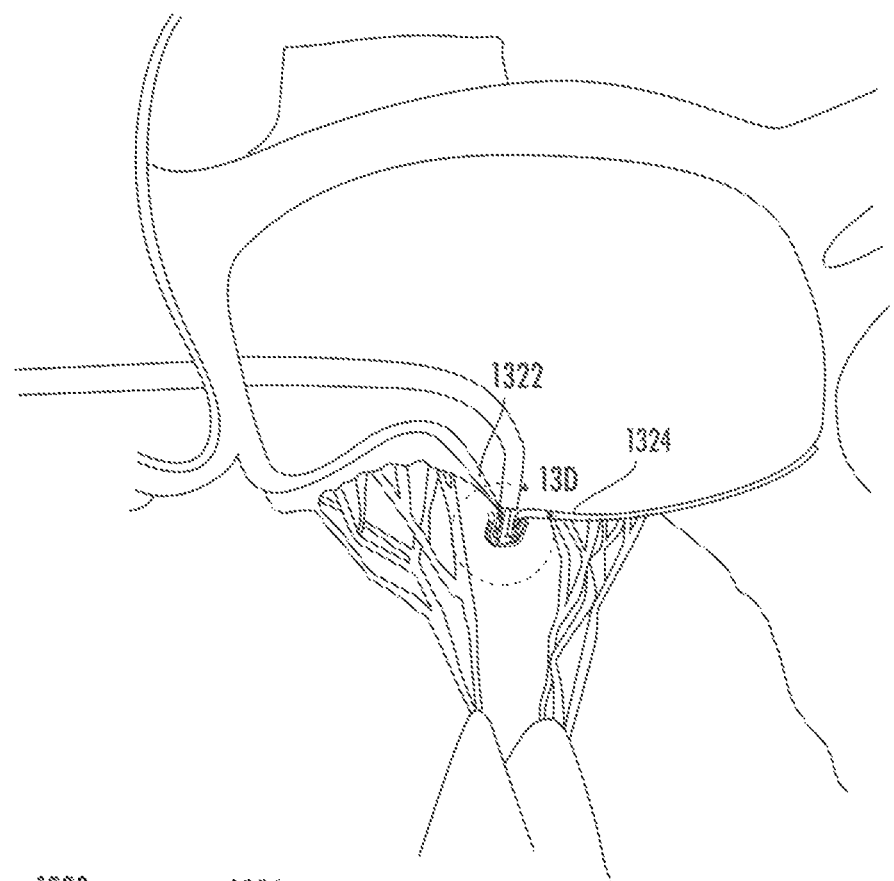

In FIG. 13A, the delivery tool 1450 is shown delivered through the atrium to the leaflets, although the disclosure is not limited to any particular delivery pathway. The rounded architecture of the delivery tool 1450 reduces the potential of interference between the chordae tendinea and the delivery tool. FIG. 13B illustrates the delivery tool 1450 following capture of a leaflet 1324 by the fixation device. Once one leaflet is captured, as shown in FIG. 13C the delivery tool 1450 may be used to pull leaflets 1324 towards leaflet 1322, for example, until the two leaflets coapt. The delivery tool 1450 may then be operated to open and close the spreader mechanism to capture the second leaflet 1322 within the retention device.

Figure 13D:
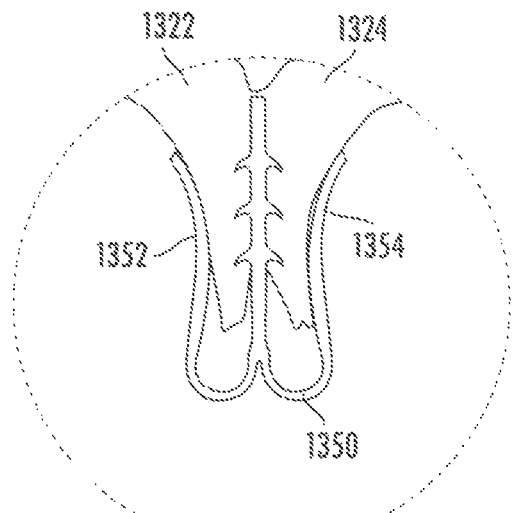
Figure 14:
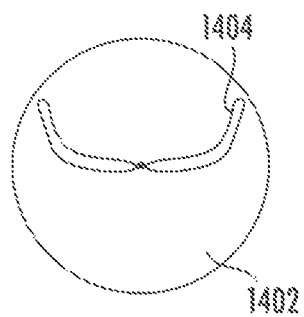
FIG. 14 is a top down view of a mitral valve following delivery of a leaflet fixation device as disclosed herein.

FIG. 13D is a magnified side view of the coupled leaflets shown in FIG. 13C, following removal of the delivery tool. As shown in FIG. 13D, following delivery, the fixation device 1350 is positioned such that the leaflets 1322, 1324 are securely captured between the proximal end 1310 of the fixation device 1350 and the arms 1352, 1354 of the fixation device 1350. FIG. 14 is a top down view of a mitral valve, following placement of a fixation device 1450 between a posterior leaflet 1402 and an anterior leaflet 1404.

Accordingly, a unitary, lightweight leaflet clip is provided for use in securing valve leaflets for cardia repair procedures has been shown and described in various embodiments. With such an arrangement, the number and type of components involved in the leaflet clipping solution is reduced to a single, unitary component that leverages the resistive forces of shape memory material as a fixation mechanism, thereby reducing the overall weight of the fixation device and failure risks associated with chronic interaction between components.

As used herein, the singular forms "a," "an," and "the" are intended to include the plural forms as well, unless the context clearly indicates otherwise. The terms "comprises" and/or "comprising," or "includes" and/or "including" when used herein, specify the presence of stated features, regions, steps, elements, and/or components, but do not preclude the presence or addition of one or more other features, regions, integers, steps, operations, elements, components, and/or groups thereof.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

All numeric values are herein assumed to be modified by the term "about," whether or not explicitly indicated. The term "about," in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g. 1 to 5 includes 1, 1.5, 2, 2.75, 3, 3.80, 4, and 5).

It is noted that references in the specification to "an embodiment," "some embodiments," "other embodiments," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether explicitly described, unless clearly stated to the contrary. That is, the various individual elements described herein, even if not explicitly shown in a particular combination, are nevertheless contemplated as being combinable or arrangeable with each other to form other additional embodiments or to complement and/or enrich the described embodiment(s), as would be understood by one of ordinary skill in the art.

The devices and/or methods disclosed and claimed herein can be made and executed without undue experimentation in light of the present disclosure. While various embodiments of the devices and methods of this disclosure have been described, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A fixation device configured and sized for affixing to a heart valve leaflet, the fixation device comprising:
    a unitary elongate body having a proximal end and a distal end with a length therebetween, the proximal end having a proximal neck portion comprising a proximal tissue engaging surface, and the distal end having a distal portion with a length, a width, and a thickness, and apportioned to define a plurality of arms each extending distally away from the proximal end of the unitary elongate body to an end of the arm;

wherein:

an arm of the plurality of arms curves to extend the end of the arm proximally toward the proximal end of the unitary elongate body and is configured to have a closed configuration wherein a tissue engaging surface defined along the end of the arm is retained adjacent the proximal tissue engaging surface of the proximal neck portion by a bias force at least equal to a leaflet grasping force; and the arm of the plurality of arms is movable towards an open configuration wherein the tissue engaging surface of the arm is spaced away from the proximal tissue engaging surface of the proximal neck portion.

2. The leaflet fixation device of claim 1, wherein each arm of the plurality of arms has a tissue engaging surface along an end thereof biased proximally towards a closed configuration adjacent to the proximal neck portion of the unitary elongate body.

3. The leaflet fixation device of claim 2, wherein, in the closed configuration, a first arm of the plurality of arms is adjacent to a first proximal tissue engaging surface of the proximal neck portion of the unitary elongate body and a second arm of the plurality of arms is adjacent to a second, opposing proximal tissue engaging surface of the proximal neck portion of the unitary elongate body.

4. The leaflet fixation device of claim 1, wherein the proximal neck portion, the distal portion, or both include a tissue retention feature configured to penetrate but not puncture tissue, puncture tissue or both.

5. The leaflet fixation device of claim 4, wherein the tissue retention feature is one of a plurality of tissue retention features disposed on the proximal neck portion, the distal portion or a combination of the proximal neck portion and the distal portion.

6. The leaflet fixation device of claim 4, wherein the tissue retention feature includes a barb, a hook, a tooth, a tine or a combination thereof.

7. The leaflet fixation device of claim 4, wherein the tissue retention feature comprises a feature that promotes tissue ingrowth into the unitary elongate body.

8. The leaflet fixation device of claim 1, wherein each arm of the plurality of arms is configured to move independently from other arms of the plurality of arms.

9. The leaflet fixation device of claim 1, wherein a weight of the leaflet fixation device is between 50-150 milligrams.

10. The leaflet fixation device of claim 1, wherein the unitary elongate body comprises a length and a width, and the distal portion of the unitary elongate body is apportioned along its thickness or along its width to define the plurality of arms.

11. The leaflet fixation device of claim 1, wherein the proximal neck portion is apportioned into a plurality of necks, and wherein the unitary elongate body comprises a biased configuration wherein at least one arm is adjacent to at least one neck.

12. A system comprising:

a heart valve leaflet fixation device having a proximal end and a distal end and comprising:

a unitary elongate body having a first end, a distal end, a first surface extending between the first end and the second end and facing a first direction, and a second surface extending between the first end and the second end and facing a second direction opposite the first direction, the body further comprising a proximal neck portion formed along the proximal end of the fixation device and having a first proximal tissue engaging surface along the first surface, and a first arm having a tissue engaging surface along the first surface and extending distally away from the proximal neck portion and then curving to extend proximally toward the proximal neck portion, wherein the first arm is biased towards a closed configuration with a bias force at least equal to a leaflet grasping force retaining the tissue engaging surface of the first arm adjacent to the first proximal tissue engaging surface of the proximal neck portion; and a delivery tool including a spreader mechanism configured to independently translate the first arm between a closed configuration in which the tissue engaging surface of the first arm is retained adjacent to the proximal tissue engaging surface of the proximal neck portion by a bias force, and an open configuration in which the tissue engaging surface of the first arm is spaced away from the proximal tissue engaging surface of the proximal neck portion.

13. The system of claim 12, wherein the proximal neck portion has a second proximal tissue engaging surface along the second surface, and the body further comprises a second arm having a second tissue-engaging surface along the second surface, the second arm extending distally away from the proximal neck portion and then curving to extend proximally towards the proximal neck portion, wherein the second arm is biased proximally towards a closed configuration with a bias force at least equal to a leaflet grasping force retaining the second distal tissue engaging surface adjacent to the second proximal tissue engaging surface of the proximal neck portion.

14. The system of claim 12, wherein the spreader mechanism comprises:

a jaw, pivotably coupled to a distal end of the delivery tool, the jaw including a coupler configured to releasably couple the first arm to the jaw;

wherein rotation of the jaw in a first direction pulls the first arm away from the proximal neck portion of the leaflet fixation device to the open configuration to provide a space therebetween configured for valvular tissue; and wherein rotation of the jaw in a second direction returns the first arm to the closed configuration.

15. The system of claim 12, wherein the spreader mechanism includes:

a spreader arm, rotatably coupled to a distal end of the delivery tool, the spreader arm disposed to push the first arm away from the proximal neck portion of the leaflet fixation device to the open configuration when rotated in a first direction to provide a space therebetween configured for valvular tissue; and wherein rotation of the spreader arm in a second direction returns the first arm to the closed configuration.

16. The system of claim 12, wherein the proximal neck portion, the first arm, or both include a tissue retention feature configured to penetrate but not puncture tissue, puncture tissue, or both, and the spreader mechanism is configured to independently translate the first arm between the closed configuration and the open configuration and to inhibit engagement between a tissue engagement feature and tissue during placement of the leaflet fixation device.

17. A fixation device configured and sized for affixing to a heart valve leaflet and having a proximal end and a distal end, the fixation device comprising:

a unitary elongate body having a first end, a second end, a first surface extending between the first end and the second end and facing a first direction, and a second surface extending between the first end and the second end and facing a second direction opposite the first direction, the body further comprising a proximal neck portion formed along the proximal end of the fixation device and having a first proximal tissue engaging surface along the first surface, and a first arm having a first tissue engaging surface along the first surface;

wherein the first arm extends distally away from the proximal neck portion and then curves to extend proximally toward the proximal neck portion, and is biased towards a closed configuration with a bias force at least equal to a leaflet grasping force retaining the first tissue engaging surface of the first arm adjacent to the first proximal tissue engaging surface of the proximal neck portion.

18. The leaflet fixation device of claim 17, wherein:

the proximal neck portion has a second proximal tissue engaging surface along the second surface; and the body further comprises a second arm having a second tissue engaging surface along the second surface and biased proximally towards a closed configuration with the second tissue engaging surface of the second arm adjacent to the second proximal tissue engaging surface of the proximal neck portion.

19. The leaflet fixation device of claim 17, wherein the proximal neck portion has a second proximal tissue engaging surface along the second surface, and the body further comprises a second arm having a second tissue-engaging surface along the second surface and extending distally away from the proximal neck portion and then curving to extend proximally toward the proximal neck portion, wherein the second arm is biased proximally towards a closed configuration with a bias force at least equal to a leaflet grasping force retaining the second tissue engaging surface of the second arm adjacent to the second proximal tissue engaging surface of the proximal neck portion.

20. The system of claim 17, wherein the proximal neck portion, the first arm, or both include a tissue retention feature configured to penetrate but not puncture tissue, puncture tissue, or both.

* * * * *